United States Patent
Weitzig et al.

(10) Patent No.: US 10,434,304 B2
(45) Date of Patent: Oct. 8, 2019

(54) IMPLANTABLE ELECTRICAL LINE

(71) Applicant: Biotronik SE & Co. KG, Berlin (DE)

(72) Inventors: Pierre Weitzig, Irrel (DE); Michael Friedrich, Kleinmachnow (DE); Jens Rump, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 260 days.

(21) Appl. No.: 15/670,766

(22) Filed: Aug. 7, 2017

(65) Prior Publication Data
US 2017/0333697 A1 Nov. 23, 2017

Related U.S. Application Data

(62) Division of application No. 14/855,253, filed on Sep. 15, 2015, now abandoned.

(60) Provisional application No. 62/064,486, filed on Oct. 16, 2014.

(51) Int. Cl.
*A61N 1/08* (2006.01)
*A61N 1/05* (2006.01)

(52) U.S. Cl.
CPC .............. *A61N 1/056* (2013.01); *A61N 1/08* (2013.01); *A61N 1/086* (2017.08)

(58) Field of Classification Search
CPC ......... A61N 1/08; A61N 1/086; A61N 1/3718
See application file for complete search history.

(56) References Cited

U.S. PATENT DOCUMENTS

| | | |
|---|---|---|
| 6,421,567 B1 | 7/2002 | Witte |
| 2010/0331942 A1* | 12/2010 | Cholette .............. A61N 1/0563 607/127 |
| 2011/0015713 A1 | 1/2011 | Min |
| 2011/0034979 A1 | 2/2011 | Min et al. |
| 2011/0125240 A1 | 5/2011 | Zhao et al. |
| 2011/0152990 A1 | 6/2011 | Shehada et al. |
| 2013/0338747 A1 | 12/2013 | Kondabatni et al. |

FOREIGN PATENT DOCUMENTS

WO 2014164972 A1 10/2014

OTHER PUBLICATIONS

European Search Report received from EP Application Serial No. 15184816.5, dated Feb. 25, 2016, 8 Pages.

* cited by examiner

*Primary Examiner* — Eugene T Wu
(74) *Attorney, Agent, or Firm* — Arc IP Law, PC; Joseph J. Mayo

(57) ABSTRACT

Embodiments include an implantable electrical line with at least one helically wound electrical conductor, an electrically conductive sleeve electrically connected to the electrical conductor, and an electrical filter. The electrical filter is arranged between a proximal and a distal longitudinal portion of a helix formed by the at least one helically wound electrical conductor as viewed in a longitudinal direction of the implantable electrical line, and is also arranged within the electrically conductive sleeve as viewed in a radial direction of the implantable electrical line.

14 Claims, 7 Drawing Sheets

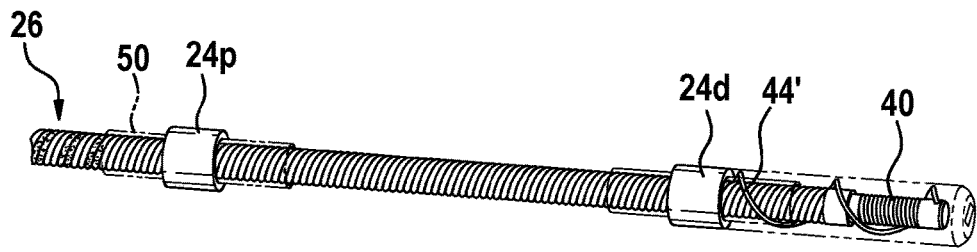
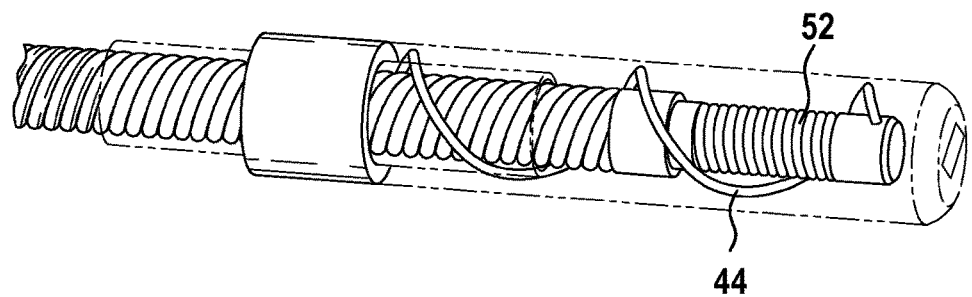
FIG. 4
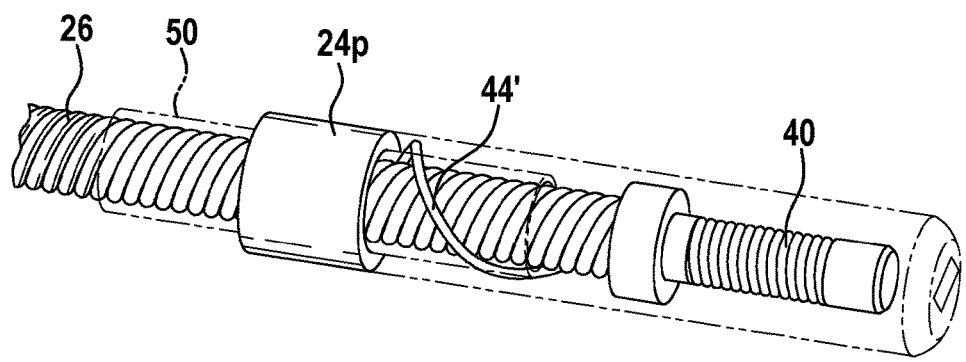
FIG. 5

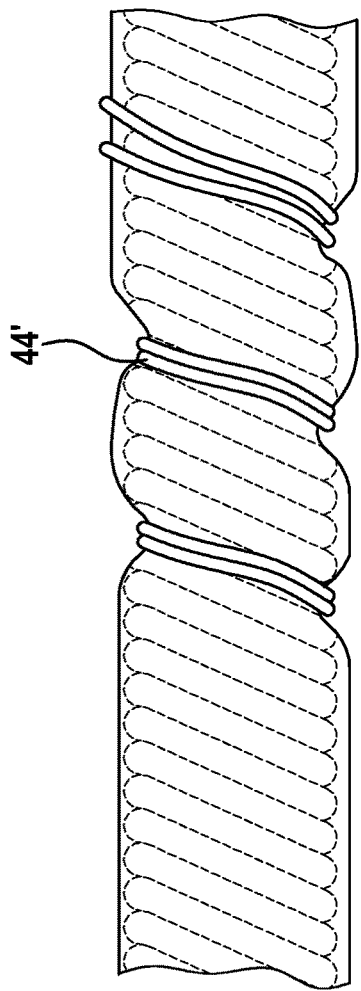
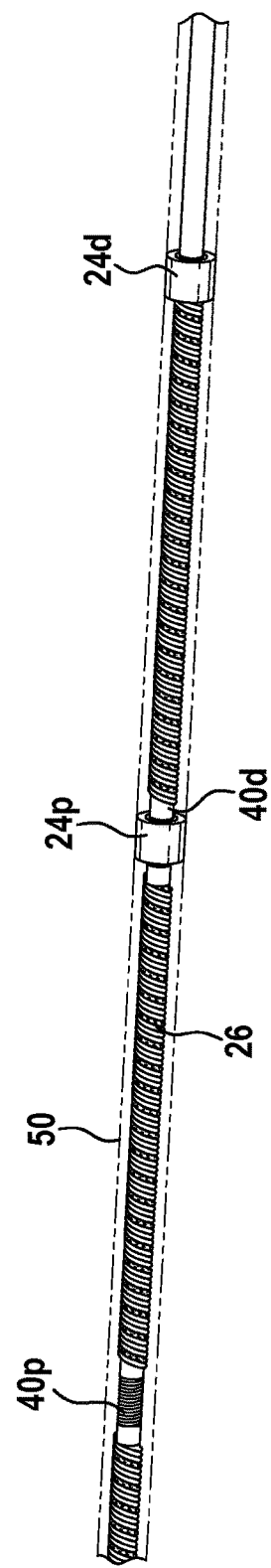

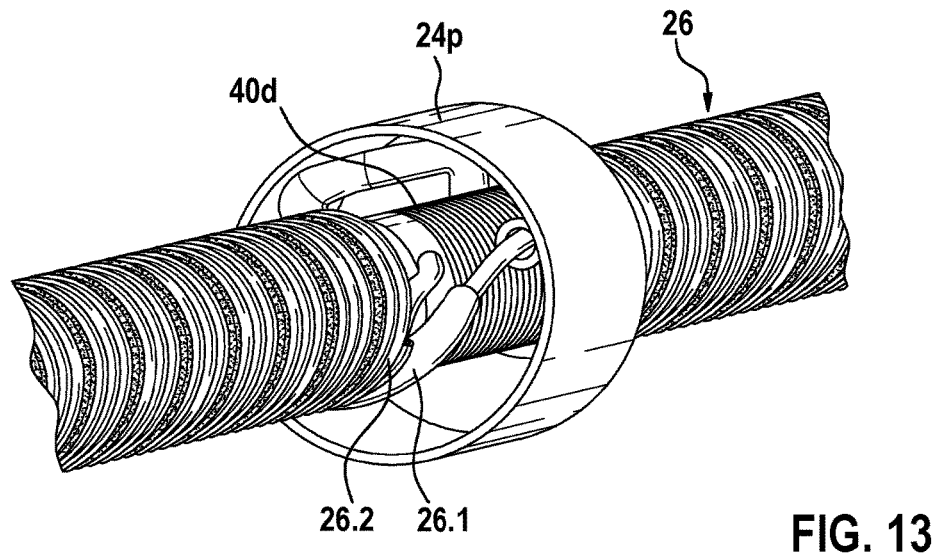
FIG. 13
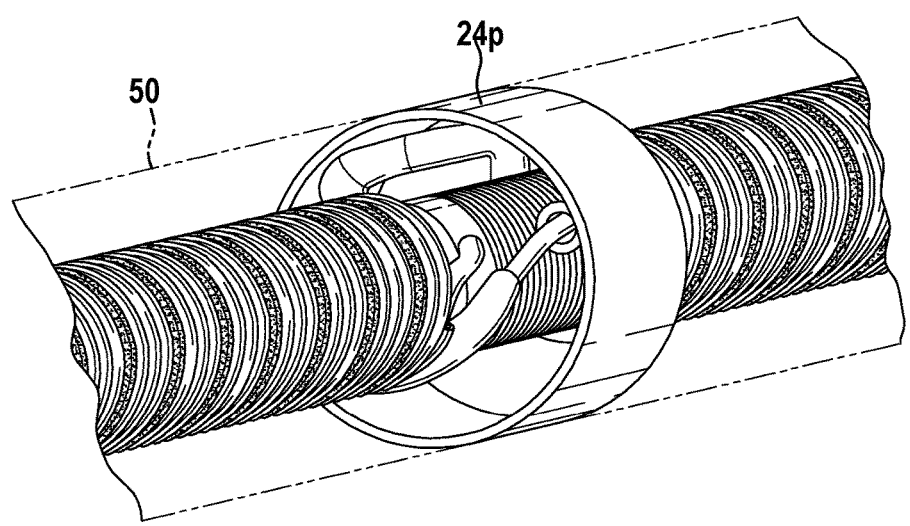
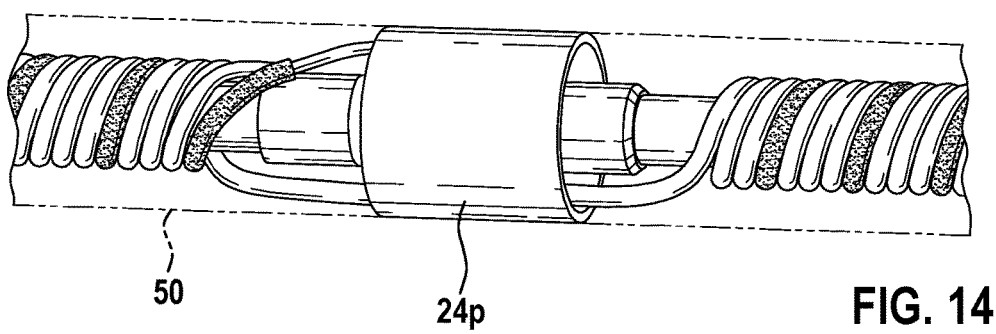
FIG. 14

IMPLANTABLE ELECTRICAL LINE

This application is a divisional of U.S. Utility patent application Ser. No. 14/855,253 filed on 15 Sep. 2015, which claims the benefit of U.S. Provisional Patent Application 62/064,486 filed on 16 Oct. 2014, the specifications of which are hereby incorporated herein by reference.

BACKGROUND OF THE INVENTION

Field of the Invention

Embodiments of the invention generally relate to a permanently or temporarily implantable medical device that includes an elongate electrical conductor, specifically an implantable electrical line with an electrical filter to avoid radio frequency-induced heating.

Description of the Related Art

Such devices, for example electrode lines for electrostimulation, generally have the disadvantage that their electrical conductor may heat up in a magnetic resonance imaging (MRI) scanner because the alternating magnetic fields prevailing in the MRI scanner induce electrical currents in the electrical conductor that are significant. Therefore, typically, cardiac pacemaker patients nowadays cannot generally be examined in an MRI scanner or may only be examined in this way to a limited extent.

Specifically, at least one stimulation electrode line is typically connected to implantable cardiac pacemakers or defibrillators. Generally, at its proximal end intended for connection to the cardiac pacemaker or defibrillator, the at least one stimulation electrode line includes a standardized electrical terminal, and, at its distal end intended for placement in the heart, includes one or more electrode poles. Such an electrode pole is typically used to deliver electrical pulses to the tissue (myocardium) of the heart or to sense electrical fields in order to sense cardiac activity, also referred to as sensing. For this purpose, electrode poles typically form electrically conductive surface portions of an electrode line. Electrode poles are typically provided as ring electrodes in the form of a ring around the electrode line or in the form of a point electrode or tip electrode at the distal end of the electrode line. The electrode poles are generally electrically conductively connected via one or more electrical conductors to contacts of the electrical terminal of the electrode line at the proximal end thereof. One or more electrical conductors, which electrically connect one or more of the electrode poles to one or more of the contacts, thus typically run between the contacts of the electrical terminal of the electrode lines at the proximal ends thereof and the electrode poles at the distal end of the electrode line. These electrical conductors, generally, may be used on the one hand for transmission of stimulation pulses to the electrode poles and on the other hand for transmission of electrical signals, received by means of the electrode poles, to the proximal end of the electrode line, also be referred to herein as a function line. Such function lines are typically electrical conductors necessary for the functions of the respective electrode line and as such are exposed to the risk that electrical currents are induced therein as a result of external alternating magnetic fields. The electrical currents for example may typically lead to an undesirable heating of the function lines or of the electrode poles connected thereto, or may lead to the delivery of corresponding currents via the electrode poles to surrounding tissue and therefore to a heating of the surrounding tissue.

Implantable lines, generally, as are used inter alia as electrode lines for cardiac pacemakers, act similarly to an antenna when exposed to irradiation of electromagnetic waves and may convert the absorbed energy into heat. Typically, the heating occurs preferably at line ends, which may lead to tissue damage. By means of a band-stop filter (or other electrical filter) connected electrically in series to the electrode pole and mechanically located either proximally or distally in relation thereto, electrical waves in the radiofrequency range are generally reflected and the heating of the tissue at the electrode pole is thus typically reduced.

Generally, for electrode lines with coaxial coils, in which the functional conductors each form an individual helix each having a different diameter, it is known to provide a capacitively coupled shunt or in each case a band-stop filter proximally in relation to the electrode.

For multi-pole electrode lines which have a number of electrode poles which are each connected to a dedicated functional conductor with corresponding contacts of the electrical terminal of the electrode line, a line construction is typically additionally used and is also referred to as a co-radial line. Generally, the individual functional conductors are insulated from one another and are wound to form a multi-turn helix, in which the individual conductors form helices congruent with one another with identical diameter and identical pitch. Typically, the helices engage with one another such that the turns of the individual helices follow one another periodically in the longitudinal direction of the helix, similarly to thread turns of a multi-turn screw, and thus form a co-radial line coil. In particular for co-radial electrode lines, such as electrode lines with a co-radial line coil, there is no known previous satisfactory solution for producing band-stop filters.

BRIEF SUMMARY OF THE INVENTION

One or more embodiments of the invention include an improved implantable line with an electrical filter.

At least one embodiment of the invention includes an implantable electrical line having at least one helically wound electrical conductor, an electrically conductive sleeve electrically connected to the electrical conductor, and an electrical filter. In one or more embodiments, the electrical filter may be arranged between a proximal and a distal longitudinal portion of a helix formed by the at least one helically wound electrical conductor, as viewed, in a longitudinal direction of the electrical line. In at least one embodiment, the electrical filter may be arranged within the electrically conductive sleeve, as viewed, in a radial direction of the electrical line.

By way of one or more embodiments, the implantable electrical line may be a multi-pole electrode line with a plurality of electrically conductive sleeves as electrode poles. In at least one embodiment, each of the plurality of electrically conductive sleeves may be electrically connected to an electrical conductor, and wherein the electrical conductors may form a co-radial line coil.

At least one embodiment of the invention is based on the finding that one of the most effective measures against MRI heating is a band-stop filter, for example an element electrically connected between the feed line and the associated electrode pole. However, with a co-radial electrode line, there may be a lack of space, for example radially, to accommodate such a filter. For example, with a co-radial electrode line, there may be a lack of space mechanically, such as immediately proximal to the respective electrode pole, to accommodate such a filter. In addition, a filter may be required for each of the electrode poles, for example for one or more of four electrode poles. At least one embodiment of the invention may include the respective electrical filters, such as band-stop filters, provided in an axially shifted position at points that provide more space without impairing the flexibility or other functional properties of the electrode. One or more embodiments may include an electrical filter as the respective filter, for example a low-pass filter.

At least one embodiment of the invention includes a multi-pole electrode line which includes at least one electrode pole arranged furthest distally, or most distal, on the electrode line, a different electrode pole arranged furthest proximally, or most proximal, on the electrode line, and at least one middle electrode pole arranged therebetween. One or more embodiments may include a respective electrical filter, for the at least one middle electrode pole and/or the at least one most distal electrode pole, that is arranged within the electrically conductive sleeve forming the respective adjacent, next-proximal electrode pole. In at least one embodiment, a respective electrical filter for a respective electrode pole, such as at least the middle electrode pole, may not be arranged within the associated electrically conductive sleeve, but within a nearest adjacent electrically conductive sleeve. As such, in one or more embodiments, contact of a filter for an electrode pole and the associated electrically conductive sleeve is facilitated.

In at least one embodiment of the invention, the electrical filter of the most proximal electrode pole may be arranged proximally to the associated electrically conductive sleeve, such as in an area of the electrode line that may be more rigid and/or may have a greater diameter than the distal region, without impairing the other functions of the electrode line.

In one or more embodiments, the electrical filter for the most distal electrode pole may be arranged distally in relation to the distal electrode pole, for example in a flexible tip region of the electrode line.

In at least one embodiment, a respective electrically conductive sleeve may form a ring electrode of the electrode line.

At least one embodiment of the invention includes a multi-pole electrode line with a co-radial feed line structure that may include the following arrangement of the electrical filters:

the filter may be located beneath the associated ring electrode, or the filters for the middle electrode poles and/or most distal ring electrodes may be located beneath the adjacent, in each case next-proximal, ring electrode, the filter for the most proximal ring electrode may be located proximally in relation thereto, in a region of the electrode that may be more rigid and/or may be of greater diameter than the distal region, without impairing the other functions of the electrode, and the filter for the most distal electrode pole may be located distally in relation to the most distal electrode pole, in a flexible tip region of the electrode line.

In at least one embodiment, the respective electrical filter may include one or more of the following variants:

the filter may include a coil made of insulated wire, which is wound with an odd number of layers around a hollow cylindrical core in a helical manner, the filter may include a coil made of insulated wire, which is wound with an even number of layers around a hollow cylindrical core in a helical manner, the filter may include a bare or insulated wire wound in a single layer, and optionally an additional capacitive element, the filter may include a coil, which is wound in a spiraled manner around a hollow cylindrical core and which is made of a film metalized on one side, and wherein the film may include a plastic film, and the electrical filter may include or may be a band-stop filter or a low-pass filter.

By way of at least one embodiment, a respective electrical filter may be electrically connected to cut line ends of a cut conductor of a co-radial coil feed line, and wherein other conductors of the co-radial coil feed line may not be cut in the region of the electrical filter, but are passed by the electrical filter without interruption.

One or more embodiments may include a method of producing an electrode line with at least one electrode pole and an electrical filter, wherein the method may include one or more of the following steps:

untwisting the co-radial coil feed line at the location of the electrode pole, cutting a conductor of the co-radial coil feed line, such that cut line ends are produced, freeing the cut line ends from insulation, inserting an electrical filter where the co-radial coil feed line is unraveled, electrically contacting the electrical filter with the ends of the cut conductor freed from insulation, sliding on an electrically conductive sleeve forming a subsequent electrode pole, such that the electrical filter is ultimately located within the electrically conductive sleeve, contacting the electrically conductive sleeve, and insulating exposed wires and contact points in the region of the electrode pole.

In at least one embodiment of the invention, advantages may be attained with an electrode line as discussed herein.

For example, in one or more embodiments, an advantage may include wherein space is created to accommodate and include a band-stop filter whilst maintaining the favorable flexibility in other portions of the electrode body.

For example, in at least one embodiment, an advantage may include placement of a distal electrical filter in the distal end of the electrode line, wherein a flexible distal end without electrode poles may be required to avoid phrenic nerve stimulation, which may occur otherwise if the ring electrodes are positioned too far distally.

BRIEF DESCRIPTION OF THE DRAWINGS

The above and other aspects, features and advantages of at least one embodiment of the invention will be more apparent from the following more particular description thereof, presented in conjunction with the following drawings, wherein:

FIG. 4 shows a distal end of a co-radial coil feed line.

FIG. 5 shows a distal end of a co-radial coil feed line.

FIG. 6 shows a detail of a co-radial coil feed line.

FIG. 7 shows a distal end of a two-pole electrode line.

FIG. 13 shows a co-radial coil feed line with a slid-on electrically conductive sleeve.

FIG. 14 shows a detail of a finished co-radial coil feed line.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
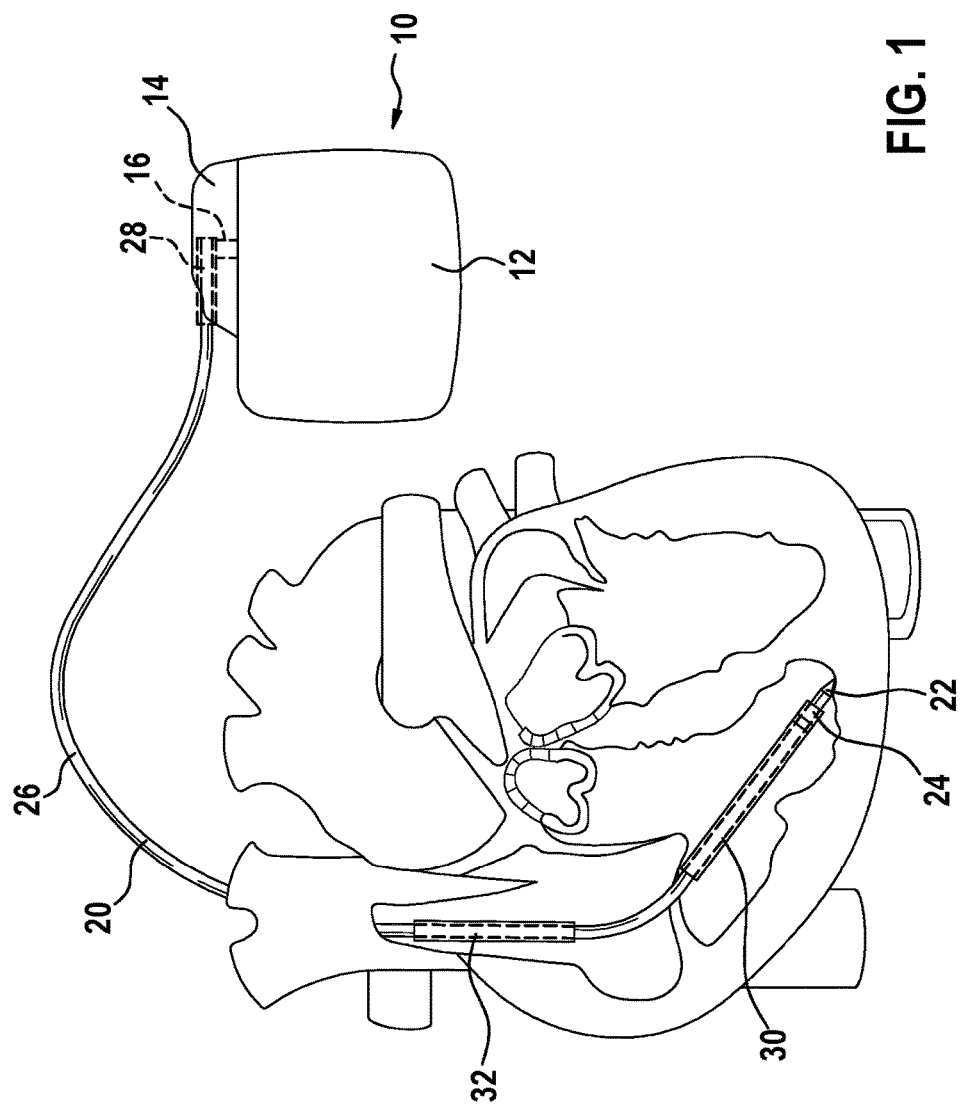
FIG. 1 shows, as implantable medical devices, an implantable heart stimulator and an implantable electrode line connected thereto.
Figure 2:
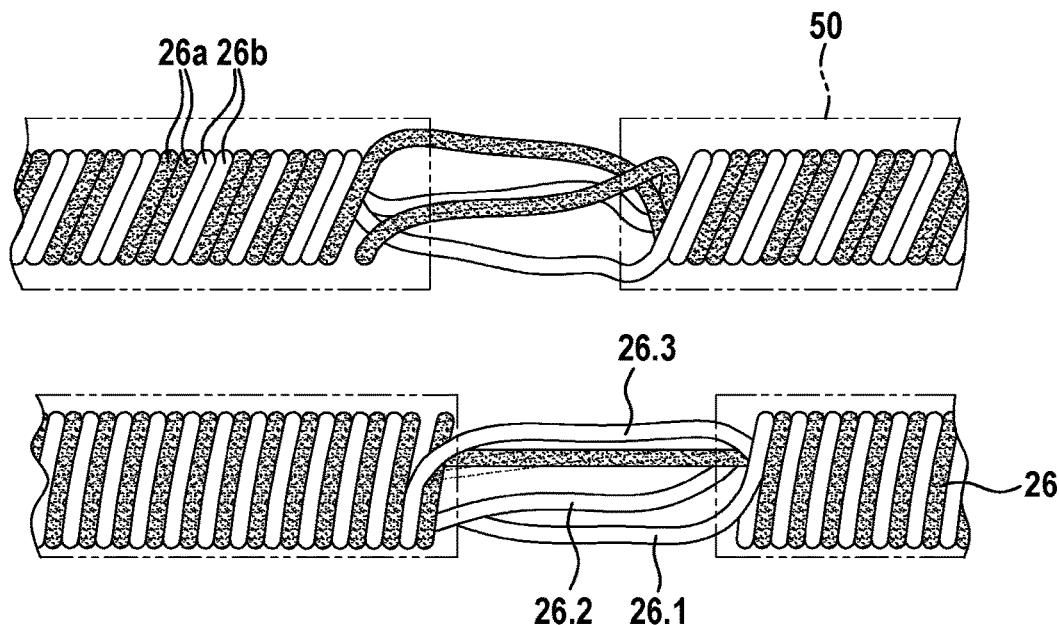
FIG. 2 shows details of a co-radial coil feed line prior to installation of a filter.

FIG. 1 shows, as implantable medical devices, an implantable heart stimulator 10 and an implantable electrode line 20 connected thereto, according to one or more embodiments of the invention. FIG. 2 shows details of a co-radial coil feed line prior to installation of a filter, according to one or more embodiments of the invention. As shown in FIG. 1, in at least one embodiment, the implantable heart stimulator 10 may be a cardiac pacemaker or a cardioverter/defibrillator (ICD). In at least one embodiment, the heart stimulator 10 may be a ventricular cardiac pacemaker and defibrillator. In one or more embodiments, the heart stimulator 10 may include dual-chamber cardiac pacemakers to stimulate the right atrium and the right ventricle, or biventricular cardiac pacemakers, which may also stimulate the left ventricle in addition to the right ventricle.

By way of at least one embodiment, the heart stimulator 10 may include a housing 12, which may include metal, which may be electrically conductive and which may serve as a large-area electrode pole. In one or more embodiments, a terminal housing 14 may be fastened to the outer face of the housing 12, also referred to herein as a header. In at least one embodiment, such a header may include contact sockets that receive plug contacts. In one or more embodiments, the contact sockets may include electrical contacts 16, which may be connected via corresponding conductors to an electronics unit arranged in the housing 12 of the heart stimulator 10.

By way of one or more embodiments, the electrode line 20 may constitute an implantable medical device in general and an implantable electrical line in particular. In at least one embodiment, electrode poles in the form of a point or tip electrode 22 and a ring electrode 24 arranged in the vicinity thereof may be arranged at the distal end of the electrode line 20. In one or more embodiments, the electrode poles 22 and 24 may be used, depending on the function of a heart stimulator to which the electrode line 20 is connected, to sense electrical potentials of the heart tissue, or myocardium, or to deliver electrical signals, for example to deliver stimulation pulses to the surrounding heart tissue. FIG. 1 shows how the electrode poles, such as the tip electrode 22 and the ring electrode 24, in the event of use of the electrode line 20, may be located in the apex of the right ventricle of a heart, according to one or more embodiments of the invention. In at least one embodiment of the invention, the electrode line 20 may include an electrically insulating sleeve 50.

In at least one embodiment, both the tip electrode 22 and the ring electrode 24 may be electrically connected in each case via at least one electrical conductor 26.1 and 26.2, and/or 26.3, to a plug contact 28 at the proximal end of the electrode line 20. In one or more embodiments, the electrical conductors together may form a co-radial coil feed line 26. In at least one embodiment, the plug contact 28 may include electrical contacts that correspond to the electrical contacts 16 of the contact socket in the terminal housing 14 of the implantable heart stimulator 10. In one or more embodiments, the electrical conductors 26 in the electrode line 20 may be formed as approximately elongate cable conductors or as helically coiled conductors. In at least one embodiment, such conductors, which electrically conductively connect the functional electrode poles to electrical contacts of the plug contact at the proximal end of the electrode line 20, will also be referred to herein as function conductors. In one or more embodiments, for example, the function conductors may transmit electrical signals, used to provide therapy, from the plug contact to the respective electrode pole, or may guide sensed signals representing electrical potentials from the respective electrode pole to the plug contact, and as such may be used during the basic function of the medical device.

By way of at least one embodiment, the electrical conductors 26, which connect the electrode poles 22 and 24 to the electrical contacts of the plug 28 of the electrode line 20, may be surrounded over the majority of their length by an insulating sleeve, such that electrical contact with the tissue of the heart is produced selectively via the electrode poles 22 and 24.

In one or more embodiments, besides the electrode poles 22 and 24, which may be used to stimulate the heart tissue, such as by ventricular stimulation, the electrode line 20 may include two electrode poles 30 and 32. In at least one embodiment, the two electrode poles 30 and 32 may have a greater area than the electrode poles 22 and 24, may be used as defibrillation electrodes, and may be formed by at least one bare helically wound wire.

It should be noted wherein one or more embodiments are explained within the scope of this invention on the basis of a right-ventricular cardiac pacemaker and defibrillator. However, at least one embodiment of the invention may include an ablation electrode line, for example, as the medical device, wherein the ablation electrode line, in the event of use, may protrude into the heart of a patient, and may be controlled by a device arranged outside of the patient and be connected thereto.

FIG. 1 shows an electrode line 20 with two electrode poles 22 and 24, of which the electrode pole 24 is a ring electrode, according to one or more embodiments of the invention. At least one embodiment of the invention may include electrode lines that have a plurality of electrode poles in the form of ring electrodes.

In order to avoid the problems as described in the Description of the Related Art above, for example in order to avoid a heating of the electrode poles, one or more embodiments of the invention include an electrical filter 40 that may be associated with each electrode pole, and may include or may be a band-stop filter or a low-pass filter. FIGS. 2 to 14, in at least one embodiment, show how, for example with co-radial electrode lines, the electrical filters 40 may be arranged and electrically connected to a respective electrode pole.

As discussed above, in at least one embodiment, the respective electrical filter may include one or more of the variants. In one or more embodiments, an electrical filter may include a metallic wire or a metallic film, which is wound such that a resultant inductance and a capacitance, such as a parasitic capacitance, form a band-stop filter or a low-pass filter. In at least one embodiment, the resonance frequency or stop frequency of the band-stop filter or the low-pass filter may be close to the frequency of an anticipated interfering electromagnetic field, such as at the frequency of the electrical fields generated by a magnetic resonance imaging (MRI) device. In one or more embodiments, the electrical filter 40 may include a coil made of a film metalized on one side, which is wound around a hollow cylindrical core in a spiraled manner, wherein an additional capacitive element may be included and may be electrically connected in parallel to the inductor, if the parasitic capacitance through the capacitor formed by the metalized film is insufficient to attain a desired resonance frequency.

One or more embodiments of the electrical filter may include a central lumen, though which a stylet or guide wire may be slid. In at least one embodiment, a respective electrical filter may be installed in an electrode body of the electrode line such that the electrical filter is protected against additional load, for example against cyclical bending.

In order to install an electrical filter 40 in an electrode line, for example a co-radial electrode line, such that the diameter and rigidity thereof do not suffer and the electrical filter is simultaneously protected, one or more embodiments of the invention may include a respective electrical filter 40 arranged beneath an electrically conductive sleeve, for example to form a ring electrode pole 24. As such, in at least one embodiment, as illustrated in FIG. 2, a co-radial coil feed line 26 may be untwisted at a location at which an electrical filter 40 may be mounted, such that initially the helix shape of the co-radial coil feed line is interrupted at the location, without severing the electrical conductors themselves.

As shown in FIG. 2, at least one embodiment may include a co-radial coil feed line, in which two double lines, a light line and a dark line, are connected to form a co-radial coil. In one or more embodiments, with the co-radial coil feed line, the two dark conductors 26*a* may contact a first electrode pole, and the two light conductors 26*b* may contact a second electrode pole. In at least one embodiment of the invention, one of the two electrode poles 24 may be located in the finished state of the electrode line at the location illustrated in FIG. 2, at which the helix shape of the co-radial coil feed line is interrupted. It is noted wherein FIG. 2 does not show an image of the finished electrode line 20.

Figure 3:
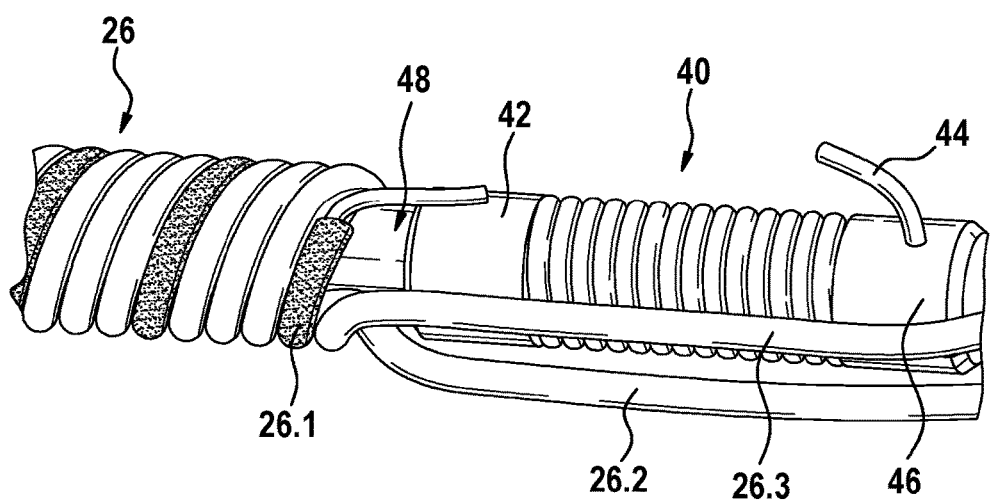
FIG. 3 shows details of a co-radial coil feed line following installation of the filter.

FIG. 3 shows details of a co-radial coil feed line following installation of the filter, according to one or more embodiments of the invention. FIG. 3 shows how, in at least one embodiment, after untwisting the co-radial coil feed line, an electrical filter 40 may be arranged in the untwisted portion of the co-radial coil feed line. By way of one or more embodiments, in order to contact the electrical filter 40, one of the conductors 26, shown as a dark conductor in FIG. 3, may be interrupted and a stripped end of the conductor may be connected to a proximal connection sleeve 42 of the electrical filter 40, for example by welding. At least one embodiment of the invention may include a further wire 44, wherein a second connection sleeve 46 at the other end of the electrical filter 40 may be connected to an electrically conductive sleeve forming an electrode pole. In one or more embodiments, the electrically conductive sleeve may be slid over the electrical filter 40 illustrated in FIG. 3, and may be electrically connected to the wire 44. In at least one embodiment, the electrical filter 40 may be located within the electrically conductive sleeve forming the electrode pole with which the electrical filter 40 is associated.

To insert the electrical filter 40, by way of at least one embodiment, an auxiliary element 48, for example a plastic tube that may be made of polyimide, may be introduced into the central lumen of the co-radial coil feed line and of the electrical filter 40, to hold the electrical filter 40 in place and to stabilize the electrical filter until the electrode line 20 is finished. In at least one embodiment, the plastic tube 48 may then remain in place or may be removed.

For example, the connection of an electrically conductive sleeve to an accordingly short wire, such as the wire 44, within the electrically conductive sleeve may be difficult. As such, at least one embodiment may include a respective electrically conductive filter 40 provided within an adjacent electrically conductive sleeve, for example not beneath the electrically conductive sleeve forming the electrode pole with which the electrical filter 40 is associated. In one or more embodiments, the respective electrical filter 40 may be electrically connected to the conductor 26 leading to an adjacent electrically conductive sleeve and not the electrically conductive sleeve within which the electrical filter 40 is arranged. The method of producing an electrode line, as discussed herein, will be described in greater detail below regarding FIGS. 7 to 14.

As discussed above, at least one embodiment of the invention may include a respective electrical filter 40 for a proximal electrode pole that may be arranged proximally to the electrode pole, wherein alternative stiffening support elements that stabilize the filter may also be arranged in the region of an electrode line.

By way of one or more embodiments, with a most distal ring electrode pole 24, the associated electrical filter 40 may be attached not within the electrically conductive sleeve forming the most distal ring electrode pole, but at a further distally arranged location of the electrode line 20. In at least one embodiment, a corresponding conductor 26 which, in the case of an electrode line, may directly contact the electrical sleeve of the distal ring electrode pole, may be continued a few millimeters, and may be contacted with a connection sleeve 42, such as a proximal connection sleeve, of the corresponding electrical filter 40. In one or more embodiments, the corresponding distal connection sleeve 46 of the electrical filter 40 may be connected to the electrically conductive sleeve via a wire 44' returned to the electrical sleeve, for example via a loosely coiled cable; as shown in FIG. 4.

FIG. 4 shows a distal end of a co-radial coil feed line, according to one or more embodiments of the invention. As shown in FIG. 4, in at least one embodiment, the electrical filter 40 may include a wire 52, which is wound in a single layer, and a coil such that an inductance of the electrical filter 40 is formed. When the wire forming the coil and therefore the inductance of the electrical filter is not wound in a single layer or with an odd number of layers, but with an even number of layers, in one or more embodiments of the invention, both connection sleeves of the electrical filter may be provided for example at the proximal end thereof. As such, the wire 44' may only be returned over a shorter distance; as shown in FIG. 5.

In at least one embodiment of the invention, with a two-pole electrode line, in which the two electrode poles are each formed by ring electrodes, an electrical filter for the then distal electrode pole may be arranged as shown in FIG. 4 or 5. As shown in FIG. 4, the electrode line may include a proximal ring electrode pole 24p and a distal ring electrode pole 24d. In one or more embodiments, the electrical filter for the proximal electrode pole may be arranged proximally thereof, as discussed above. In at least one embodiment, no electrical filter may be arranged within an electrically conductive sleeve.

In one or more embodiments, individual conductors may be unscrewed from the co-radial coil feed line where necessary and stripped of their insulation. In at least one embodiment, winding gaps may be produced in the remaining co-radial coil feed line. In order to guide non-insulated conductors further axially along the co-radial coil feed line, in one or more embodiments, the initially remaining co-radial coil feed line with the winding gaps thereof may be coated with an insulating layer, for example a silicone tube, and the non-insulated conductors may then be wound into the winding gaps, as illustrated in FIG. 6. FIG. 6 shows a detail of a co-radial coil feed line, according to one or more embodiments of the invention.

At least one embodiment of the invention may include an additional protective tube, for example made of polyimide, which may be fitted inside the co-radial coil feed line. One or more embodiments may include a mechanically loadable and yet flexible co-radial coil feed line, which may be adapted in a versatile manner. For example, in at least one embodiment, the co-radial coil feed line may be used to contact a distally arranged electrical filter, as illustrated in FIGS. 4 and 5.

FIGS. 7 to 14 illustrate how an electrode line in accordance with at least one embodiment of the invention may be produced. In one or more embodiments, a respective electrical filter may be arranged within an electrically conductive sleeve, which is adjacent to the electrically conductive sleeve forming the electrode pole with which the electrical filter is associated, and in which the electrical filter for the most proximal electrode pole may be arranged proximally thereof.

FIG. 7 shows a distal end of a two-pole electrode line according to one or more embodiments of the invention, and shows a portion of the finished electrode line 20 from the outside. As shown in FIG. 7, in at least one embodiment, the electrode line may include a proximal ring electrode pole 24p and a distal ring electrode pole 24d. In one or more embodiments, both the proximal ring electrode 24p and the distal ring electrode 24d may be formed by or may include a respective electrically conductive sleeve, for example a metal sleeve. In at least one embodiment, the electrode line 20 between the electrode poles and either side of the electrode poles may carry an electrically insulating sleeve 50, which may be formed by or may include a silicone tube. One or more embodiments of the invention may include a co-radial coil feed line 26, which may include or may be formed by four electrical conductors 26.1, 26.2, 26.3 and 26.4, also shown in FIG. 8, that extend within the sleeve 50 and within the electrically insulating sleeves of 24p and 24d. In at least one embodiment, the associated electrical filter 40p may be arranged proximally to the proximal electrode pole 24p. In one or more embodiments, the electrical filter 40d for the distal electrode pole 24d may be arranged within the electrically conductive sleeve of the proximal electrode pole 24p.

By way of one or more embodiments, shown in FIGS. 8 to 13, one of the four conductors 26.1, 26.2, 26.3 and 26.4 of the co-radial coil feed line 26 is illustrated as dark, whereas the other three conductors are illustrated as light.

Figure 8:
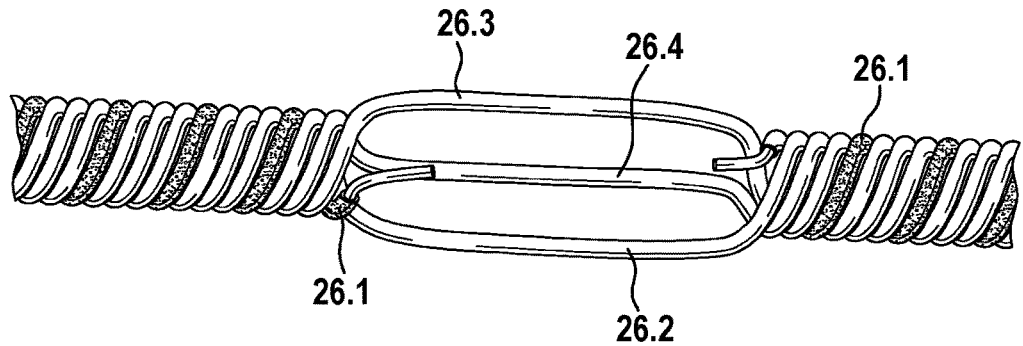
FIG. 8 shows details of a co-radial coil feed line prior to installation of the filter.
Figure 9:
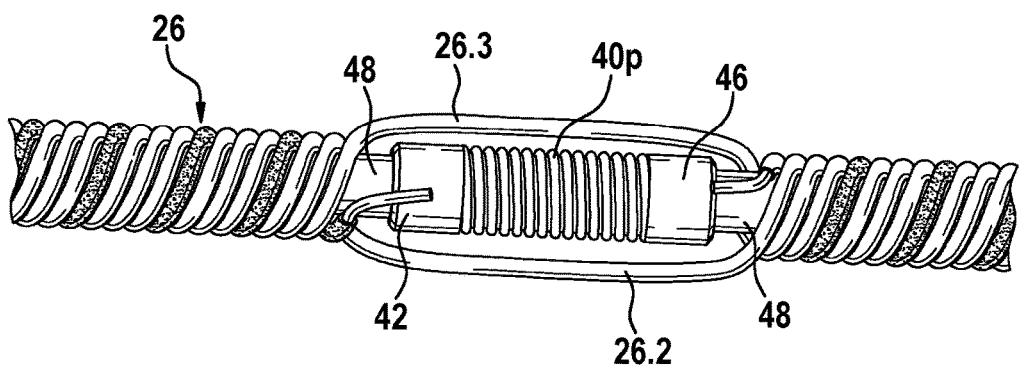
FIG. 9 shows details of a co-radial coil feed line following installation of the filter.
Figure 10:
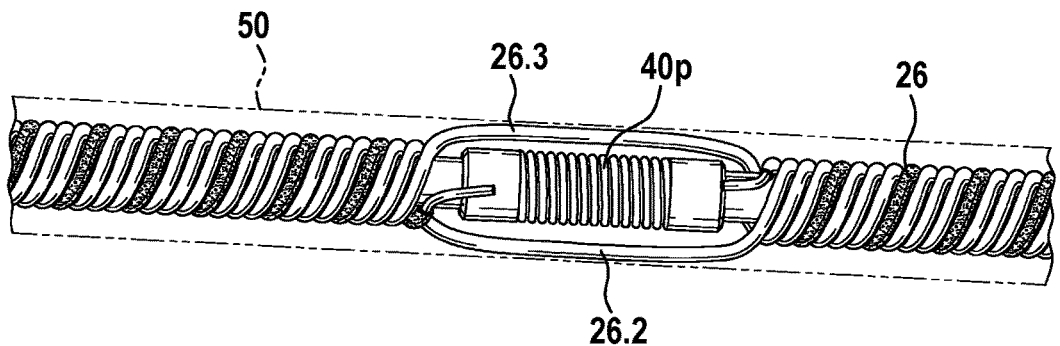
FIG. 10 shows a co-radial coil feed line with a fitted insulating sleeve.

FIG. 8 shows details of a co-radial coil feed line prior to installation of the filter and FIG. 9 shows details of a co-radial coil feed line following installation of the filter, according to one or more embodiments of the invention. FIGS. 8 and 9, in at least one embodiment, depict the installation of the proximal filter 40p. In one or more embodiments, the co-radial coil feed line 26 may first be untwisted where the proximal electrical filter 40p is to be arranged, and the electrical conductor 26.1 associated with the proximal electrode pole 24p may be cut. In at least one embodiment, the other electrical conductors 26.2, 26.3 and 26.4 may not be cut and may remain insulated. In one or more embodiments, the cut ends of the conductor 26.1 may be freed from the insulation thereof; as shown in FIG. 8.

In at least one embodiment, the electrical filter 40p may then be inserted at the location that has become free due to the untwisting of the windings. As such, in one or more embodiments, the electrical filter 40p may first be inserted into the space and a polyimide tube 48 may then be guided through the lumen of the co-radial coil feed line 26 and the electrical filter 40p in order to hold the electrical filter 40p in place in a reliable and stable manner. In at least one embodiment, the free wire ends of the cut conductor 26.1 freed from the insulation may then be welded to the proximal connection sleeve 42 and the distal connection sleeve 46 of the electrical filter 40p and may be electrically connected as such; as shown in FIG. 9.

In one or more embodiments, the electrically insulating sleeve 50 may then be slid in the form of a silicone tube over the assembly thus produced.

Figure 11:
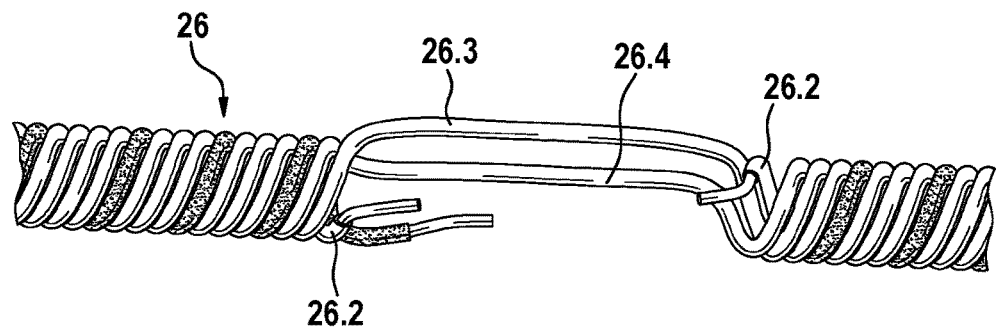
FIG. 11 shows details of a co-radial coil feed line prior to installation of the filter.

According to at least one embodiment, to install the distal electrical filter 40d, the co-radial coil feed line 26 may be untwisted at the location of the proximal electrode pole 24p, a further conductor 26.2 of the co-radial coil feed line 26 may be cut, and the cut ends may be freed from the insulation thereof. At the location of the proximal electrode pole 24p, by way of one or more embodiments, two of the conductors of the co-radial coil feed line may run without separation, whereas the conductor 26.1 that contacts the electrically conductive sleeve of the proximal electrode pole 24p may be provided with a non-insulated end, and the conductor 26.2 that contacts the distal electrode pole 24d in the region of the proximal electrode pole may include two separate line ends freed from insulation; as shown in FIG. 11.

Figure 12:
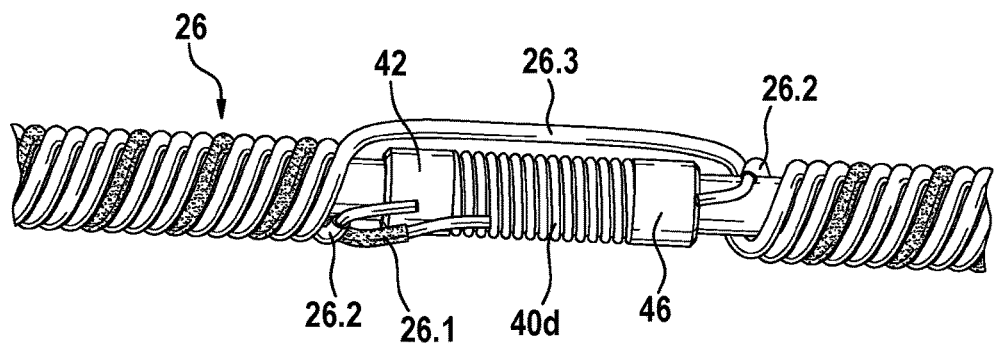
FIG. 12 shows details of a co-radial coil feed line following installation of the filter.

As discussed above regarding the proximal electrical filter 40p, in one or more embodiments, the distal electrical filter 40d may be inserted into the space created by untwisting the co-radial coil feed line 26, and the connection sleeves 42 and 46 of said filter may be electrically connected by welding to the free, cut ends of the conductor 26.2 freed from insulation; as shown in FIG. 12.

In at least one embodiment, the electrically conductive sleeve forming the proximal electrode pole 24p may then be slid onto the co-radial coil feed line 26 until directly above the electrical filter 40d; as shown in FIGS. 12 and 13. In one or more embodiments, the free end of the conductor 26.1, the dark conductor, freed from insulation may be connected to the corresponding electrically conductive sleeve 24p; as shown in FIG. 12.

In at least one embodiment, the part of the conductor 26.1, of the dark conductor in the Figures, extending distally of the proximal electrode pole 24p may not be further electrically contacted and may be used exclusively such that no winding gaps are created in the further co-radial coil feed line 26.

In order to avoid electrical short circuits, in one or more embodiments of the invention, all non-insulated wire portions and exposed contacts in the region of the electrically conductive sleeve of the proximal electrode pole 24$p$ may be insulated from one another, for example by a corresponding parylene coating, a spray-on coating or by squirting the region with silicone. In at least one embodiment, further parts of the electrically insulating outer sleeve 50 may then be fitted or slipped on in order to thus finish the electrode line 20, as illustrated in FIG. 14.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS

10—implantable heart stimulator
12—housing
14—terminal housing
16—contacts
20—electrode line
22—point or tip electrode
24—ring electrode
22, 24—electrode poles
26.1, 26.2, 26.3, 26.4—electrical conductors
26—co-radial coil feed line
28—plug contact
40—electrical filter
42—proximal connection sleeve
44—wire
46—distal connection sleeve
48—auxiliary element
50—electrically insulating sleeve
52—wire

What is claimed is:

1. An implantable electrical line comprising:
   at least one helically wound electrical conductor;
   at least one electrically conductive sleeve electrically connected to the at least one helically wound electrical conductor;
   multiple electrode poles comprising at least a distal electrode pole, a middle electrode pole and a proximal electrode pole, and wherein each electrode pole comprises an associated electrically conductive sleeve; and,
   at least one electrical filter;
   wherein the at least one electrical filter is arranged between a proximal longitudinal portion and a distal longitudinal portion of a helix formed by the at least one helically wound electrical conductor in a longitudinal direction of the implantable electrical line,
   wherein the at least one electrical filter is situated radially inward relative to a radius of the at least one electrically conductive sleeve and located anywhere axially relative to an electrode pole of the multiple electrode poles,
   wherein the at least one electrical conductive sleeve forms an electrode pole,
   wherein each of the multiple electrode poles comprises a respective filter such that the respective electrical filter for the middle electrode pole is not arranged within the associated electrically conductive sleeve associated with the middle electrode pole,
   but the respective electrical filter for the middle electrode pole is arranged within a nearest adjacent electrically conductive sleeve that forms a nearest adjacent electrode pole.

2. The implantable electrical line as claimed in claim 1, wherein the at least one electrically conductive sleeve comprises a plurality of electrically conductive sleeves as electrode poles, wherein the at least one helically wound electrical conductor comprises a plurality of helically wound electrical conductors, wherein each of the plurality of electrically conductive sleeves are electrically connected to an electrical conductor of the plurality of helically wound electrical conductors, and wherein the plurality of helically wound electrical conductors form a co-radial line coil.

3. The implantable electrical line as claimed in claim 1, wherein each electrode pole of each of the at least one electrically conductive sleeve forms a ring electrode of the implantable electrical line.

4. The implantable electrical line as claimed in claim 1, wherein the at least one electrical filter comprises a coil made of insulated wire, wherein said coil is wound with an odd number of layers around a hollow cylindrical core in a helical manner.

5. The implantable electrical line as claimed in claim 1, wherein the at least one electrical filter comprises a coil made of insulated wire, wherein said coil is wound with an even number of layers around a hollow cylindrical core in a helical manner.

6. The implantable electrical line as claimed in claim 1, wherein the at least one electrical filter comprises a bare or insulated wire wound in a single layer and a capacitive element.

7. The implantable electrical line as claimed in claim 1, wherein the at least one electrical filter comprises a coil, wherein the coil is wound in a spiraled manner around a hollow cylindrical core and wherein the coil comprises a film that is metalized on one side of the film.

8. The implantable electrical line as claimed in claim 7, wherein the film is a plastic film.

9. The implantable electrical line as claimed in claim 1, wherein the at least one electrical filter comprises a band-stop filter or a low-pass filter.

10. The implantable electrical line as claimed in claim 1, wherein the at least one helically wound electrical conductor comprises a plurality of helically wound electrical conductors that form a co-radial coil feed line,
    wherein the plurality of helically wound electrical conductors comprise a cut conductor with cut line ends and at least one other conductor that is not cut in a region of the at least one electrical filter,
    wherein the cut line ends of the cut conductor of the co-radial coil are electrically connected to the at least one electrical filter,
    wherein the at least one other conductor of the co-radial coil feed line that is not cut in a region of the electrical filter bypasses the at least one electrical filter in a non-interrupted manner, and
    wherein the at least one electrical filter that is bypassed by the at least one other conductor is a same electrical filter that is connected to the cut conductor with cut line ends.

11. An implantable electrical line comprising:
at least one helically wound electrical conductor;
at least one electrically conductive sleeve electrically connected to the at least one helically wound electrical conductor;
multiple electrode poles comprising at least a distal electrode pole, a middle electrode pole and a proximal electrode pole, and wherein each electrode pole comprises an associated electrically conductive sleeve; and,
at least one electrical filter;
wherein the at least one electrical filter is arranged between a proximal longitudinal portion and a distal longitudinal portion of a helix formed by the at least one helically wound electrical conductor in a longitudinal direction of the implantable electrical line,
wherein the at least one electrical filter is situated radially inward relative to a radius of the at least one electrically conductive sleeve and located anywhere axially relative to an electrode pole of the multiple electrode poles,
wherein the at least one electrical conductive sleeve forms an electrode pole,
wherein the distal electrode pole comprises a respective filter
such that the respective electrical filter for the distal electrode pole is not arranged within the associated electrically conductive sleeve associated with the distal electrode pole,
but the respective electrical filter for the distal electrode pole is arranged within a proximal adjacent electrically conductive sleeve that forms a proximal adjacent electrode pole.

12. The implantable electrical line as claimed in claim 11, wherein the proximal electrode pole is located at a most proximal portion of the implantable electrical line, wherein the at least one electrical filter comprises a respective electrical filter for the proximal electrode pole and associated with an electrically conductive sleeve of the at least one electrically conductive sleeve, and wherein the respective electrical filter for the proximal electrode pole is arranged proximally to the proximal electrode pole.

13. An implantable electrical line comprising:
at least one helically wound electrical conductor;
at least one electrically conductive sleeve electrically connected to the at least one helically wound electrical conductor;
multiple electrode poles comprising at least a distal electrode pole, a middle electrode pole and a proximal electrode pole, and wherein each electrode pole comprises an associated electrically conductive sleeve; and,
at least one electrical filter;
wherein the at least one electrical filter is arranged between a proximal longitudinal portion and a distal longitudinal portion of a helix formed by the at least one helically wound electrical conductor in a longitudinal direction of the implantable electrical line,
wherein the at least one electrical filter is situated radially inward relative to a radius of the at least one electrically conductive sleeve and located anywhere axially relative to an electrode pole of the multiple electrode poles,
wherein the at least one electrical conductive sleeve forms an electrode pole,
wherein the proximal electrode pole comprises a respective filter
such that the respective electrical filter for the proximal electrode pole is not arranged within the associated electrically conductive sleeve associated with the proximal electrode pole,
but the electrical filter for the proximal electrode pole is arranged within a distal adjacent electrically conductive sleeve that forms a distal adjacent electrode pole.

14. The implantable electrical line as claimed in claim 13, wherein the distal electrode pole is located at a most distal portion of the implantable electrical line, wherein the at least one electrical filter comprises an electrical filter for the distal electrode pole, and wherein the respective electrical filter for the distal electrode pole is arranged distally to the distal electrode pole.

\* \* \* \* \*